US00PP08044P

United States Patent [19]

van der Knaap

[11] Patent Number: Plant 8,044

[45] Date of Patent: Nov. 24, 1992

[54] CHRYSANTHEMUM PLANT — MUNDIAL CULTIVAR

[75] Inventor: Jacques C. M. van der Knaap, De Lier, Netherlands

[73] Assignee: Fides Beheer B.V., De Lier, Netherlands

[21] Appl. No.: 679,528

[22] Filed: Apr. 2, 1991

[51] Int. Cl.[5] ..... A01H 5/00

[52] U.S. Cl. ..... Plt./82

[58] Field of Search ..... Plt./74, 74.1, 82.4

*Primary Examiner*—Howard J. Locker

*Attorney, Agent, or Firm*—Burns, Doane, Swecker & Mathis

[57] ABSTRACT

A new and distinct cultivar of Chrysanthemum plant named Mundial is provided. The new cultivar was the result of a controlled breeding program wherein the Moneymaker cultivar (U.S. Plant Pat. No. 6,341) was pollinated by the Delta cultivar (U.S. Plant Pat. No. 5,815). More specifically, the new cultivar forms attractive relatively large light red-purple anemone-centered flowers having a green center when immature. The inflorescence tends to be pyramidal in configuration. The response period of the flowers is approximately eight weeks. The new cultivar is particularly suited for use in the production of a cut anemone spray under greenhouse conditions.

1 Drawing Sheet

SUMMARY OF THE INVENTION

The present invention comprises a new and distinct cultivar of Chrysanthemum, botanically known as *Dendranthema morifolium* Ramat., previously, *Chrysanthemum morifolium,* Ramat., and hereinafter is referred to by the cultivar name Mundial.

The new cultivar is the product of a planned breeding program which had as its objective the creation of a new Chrysanthemum cultivar which exhibits attractive relatively large light red-purple flowers having a green center when immature, exhibits a flower response period of approximately eight weeks, and possesses the ability to produce flowers of commercially acceptable quality throughout the year in a cut mum production program. Such combination of traits is not believed to have been present in the previously available Chrysanthemum cultivars. This objective was satisfactorily fulfilled in the cultivar of the present invention.

The breeding program which resulted in the production of the new cultivar of the present invention was carried out in a controlled environment during 1984 at De Lier, The Netherlands. The female parent (i.e., the seed parent) was the Moneymaker cultivar (U.S. Plant Pat. No. 6,341) and the male parent (i.e., the pollen parent) was the Delta cultivar (U.S. Plant Pat. No. 5,815). The parentage of the new cultivar can be summarized as follows:

Moneymaker × Delta.

The seeds resulting from the above pollination were sown and plantlets were obtained which were physically and biologically different from each other. Selective study resulted in the identification of a single plant of the new variety.

It was found that the new cultivar of the present invention:

(a) exhibits attractive relatively large anemone-centered flowers having an overall diameter of approximately 75 to 80 mm. wherein the ray florets are light red-purple and the disc florets are green in coloration when immature, (b) bears flowers in a somewhat pyramidal configuration, (c) exhibits a flower response period of approximately eight weeks, and (d) has the ability to produce flowers of commercially acceptable quality throughout the year in a cut mum production program.

Asexual reproduction of the new cultivar by cuttings initially taken during September, 1985, as performed at De Lier, The Netherlands, in a controlled environment has demonstrated that the characteristics of the new cultivar as herein disclosed are firmly fixed and are retained through successive generations of asexual propagation.

Mundial has not been observed under all possible environmental conditions to date. Accordingly, it is possible that the phenotype may vary somewhat with variations in the environment, such as temperature, light, day length, contact with pesticides and/or subjection to growth retardant treatments.

When the new cultivar of the present invention is compared to the Moneymaker cultivar (U.S. Plant Pat. No. 6,341), it is observed that the flower size is larger, the ray florets are light red-purple instead of light pink in coloration, the flower center tends to be slightly smaller, the plant shows less vigor, and the stems are more sturdy. Also, the Mundial cultivar tends to exhibit more variability in vase life than the Moneymaker cultivar. Otherwise, the flower type, response time, and low temperature tolerance tend to be substantially the same in each instance.

BRIEF DESCRIPTION OF THE PHOTOGRAPH

The accompanying photograph shows as nearly true as it is reasonably possible to make the same in a color illustration of this character, a typical specimen of an overall plant of the new cultivar. The plant was grown in a greenhouse at De Lier, The Netherlands.

DETAILED DESCRIPTION

The chart used in the identification of colors described hereafter is the R.H.S. Colour Chart of The Royal Horticultural Society, London, England. The color values were determined at 11:00 a.m. to 12:00 noon under natural daylight conditions at De Lier, The Netherlands, during October, 1989. The plants described were grown under standard greenhouse conditions which approximate those commonly utilized for the production of cut mums.

Classification:

*Botanical.*—*Dendranthema morifolium* Ramat., cv. Mundial.

*Commercial.*—Cut anemone spray.

Inflorescence

A. Capitulum:

*Form.*—Pyramidal.

*Type.*—Anemone.

*Diameter across face.*—Approximately 75 to 80 mm. on average.

*Diameter of disc.*—Approximately 22 to 30 mm. on average.

B. Corolla of ray and disc florets:

*Color (General tonality from a distance of three meters).*—light red-purple.

*Color ray florets.*—(Top surface).—Slightly paler than Red-Purple Group 69B.

*Color disc florets.*—Green Group 142A when immature.

C. Reproductive organs:

*Androecium.*—Not present.

*Gynoecium.*—Present in disc florets.

Plant

A. General appearance:

*Height.*—Approximately 100 cm. on average.

B. Foliage:

*Color (upper surface).*—Yellow-Green Group 147A.

*Color (under surface).*—Yellow-Green Group 147B.

I claim:

1. A new and distinct cultivar of Chrysanthemum plant named Mundial, substantially as herein shown and described, which:

(a) exhibits attractive relatively large anemone-centered flowers having an overall diameter of approximately 75 to 80 mm. wherein the ray florets are light red-purple and the disc florets are green in coloration when immature, (b) bears flowers in a somewhat pyramidal configuration, (c) exhibits a flower response period of approximately eight weeks, and (d) has the ability to produce flowers of commercially acceptable quality throughout the year in a cut mum production program.

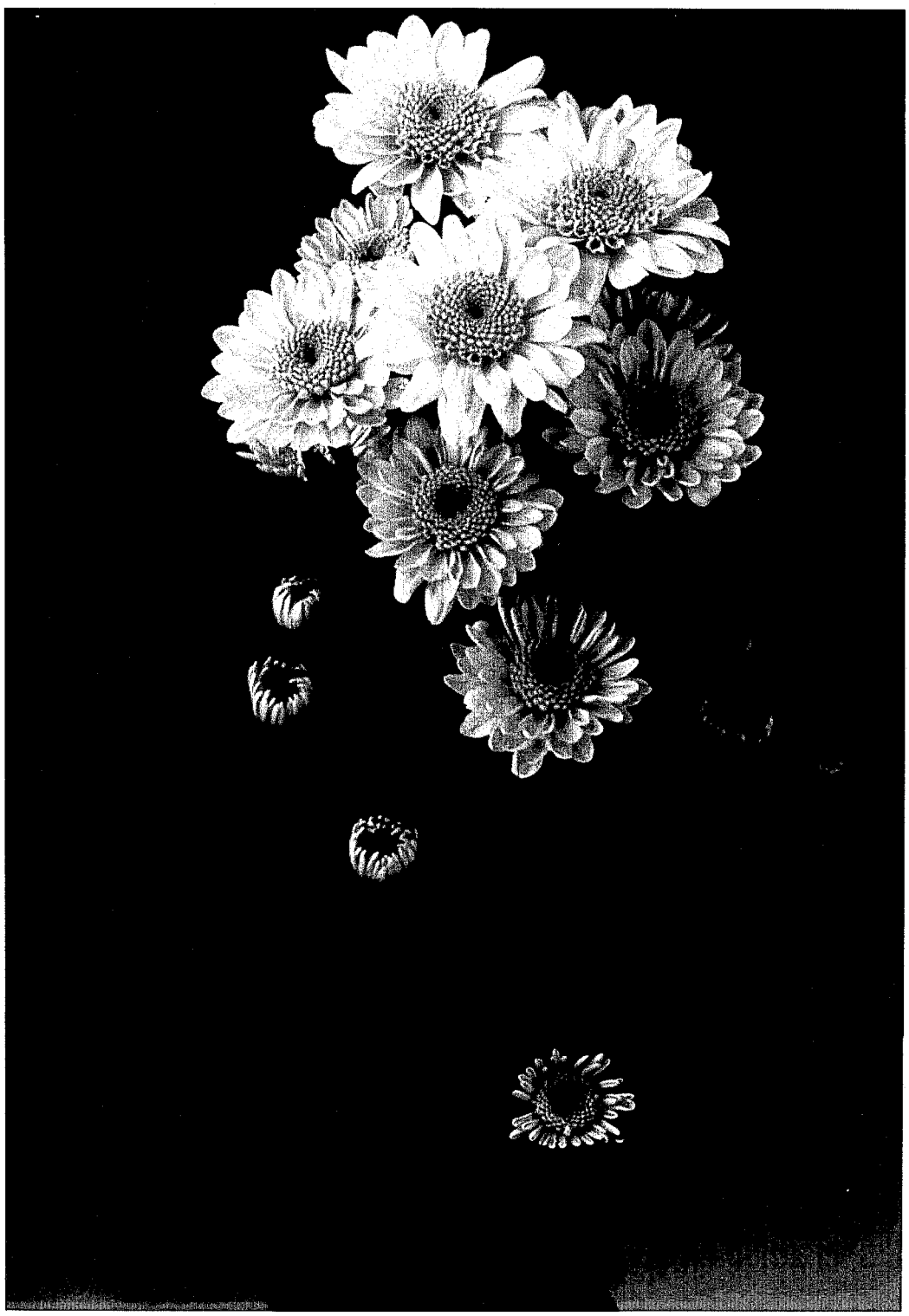

* * * * *